United States Patent
Murari et al.

(10) Patent No.: US 6,844,048 B2
(45) Date of Patent: Jan. 18, 2005

(54) SUBSTRATES FOR POWDER DEPOSITION CONTAINING CONDUCTIVE DOMAINS

(75) Inventors: Ramaswamy Murari, Hillsborough, NJ (US); Jen-Chi Chen, Morrisville, PA (US); Suggy S. Chrai, Cranbury, NJ (US)

(73) Assignee: Sarnoff Corporation, Princeton, NJ (US)

( * ) Notice: Subject to any disclaimer, the term of this patent is extended or adjusted under 35 U.S.C. 154(b) by 6 days.

(21) Appl. No.: 09/903,394

(22) Filed: Jul. 11, 2001

(65) Prior Publication Data

US 2003/0012926 A1 Jan. 16, 2003

(51) Int. Cl.[7] .............................. B05D 1/06; B32B 3/24
(52) U.S. Cl. ........................ 428/143; 428/138; 118/624; 118/625; 427/458; 427/468; 427/469; 427/475; 427/2.14; 424/489; 424/443; 424/451
(58) Field of Search ................................ 428/138, 143; 118/624, 625; 427/458, 468, 469, 475, 2.14; 424/489, 443, 451

(56) References Cited

U.S. PATENT DOCUMENTS

| | | | | |
|---|---|---|---|---|
| 4,231,660 A | | 11/1980 | Remy et al. | |
| 5,558,928 A | * | 9/1996 | DiStefano et al. | 428/209 |
| 5,669,973 A | | 9/1997 | Pletcher | |
| 6,007,630 A | * | 12/1999 | Pletcher et al. | 118/624 |
| 6,146,685 A | * | 11/2000 | Chrai et al. | 427/2.14 |
| 6,303,143 B1 | * | 10/2001 | Chrai et al. | 424/451 |
| 6,319,541 B1 | * | 11/2001 | Pletcher et al. | 427/2.14 |
| 6,380,060 B1 | * | 4/2002 | Zohni | 438/612 |
| 6,399,143 B1 | * | 6/2002 | Sun et al. | 427/2.14 |
| 6,428,809 B1 | * | 8/2002 | Abrams et al. | 424/451 |

OTHER PUBLICATIONS

International search report from International Application No. PCT/US01/41339, mailed Nov. 16, 2001.

* cited by examiner

Primary Examiner—William P. Watkins, III
(74) Attorney, Agent, or Firm—William J. Burke

(57) ABSTRACT

Provided is, among other things, a conductive inlay film comprising: a layer of dielectric film having a pattern of holes suitable to define selected regions to which particles will be deposited by electrostatic deposition; and a conductive element comprising polymer, which element comprises (a) a conductive film laminated against the dielectric film or (b) a conductive film embedded within the holes, the portion of the conductive element appearing within the holes comprising conductive inlays, wherein the conductive element is adapted to contact one or more electrode pads and provide electrical potentials at the selected regions, and wherein the dielectric film electrically isolates the selected regions.

23 Claims, 3 Drawing Sheets

SUBSTRATES FOR POWDER DEPOSITION CONTAINING CONDUCTIVE DOMAINS

The present invention relates to substrates used as the support on which powders are deposited using techniques wherein electrical forces attract the powders for localized deposition.

The applicants or those working with applicants have previously described apparatuses and techniques for using electrical forces to make controlled depositions of materials. Such depositions make it possible to deposit controlled amounts of, for example, a pharmaceutical onto spatially resolved areas of a substrate. These techniques have typically deposited charged particles or grains onto a substrate mounted on a device ("electrostatic chuck") that provides the electrical forces (e.g., electrostatic) that attracts the particles or grains. The particles or grains are typically charged, though attraction can occur through induced polarizations of the particles or grains. The electrostatic chuck has, for example, electrode pads to which electrical potentials are applied to create attractive forces. Adjacent electrodes, of a different potential, can be used to shape the attractive forces or steer particles or grains away from undesired locations. One such electrostatic chuck is illustrated in FIG. 3. Once attracted to a given location, grains or particles can induce an image force through their proximity to conductors, which image force can be a powerful contributor to the forces retaining the grains or particles. Other retentive forces include other charge and charge redistribution induced forces, packing forces and Van der Waals forces.

A limitation on this technology has been the amount of particles or grains that can be effectively directed to a given location. One source of this limitation is a practical limit to the strength and localization of the electrical forces close to a given deposition location. The present invention addresses this problem by creating substrates for the deposition having patterned inlays of conductive material, which conductive inlay material serves as an extension or adjunct to the electrode pads of the electrostatic chuck, allowing greater charge density near the site of deposition. The invention provides improved quality of the depositions and allows larger quantities to be deposited.

SUMMARY OF THE INVENTION

The invention provides, for example, a conductive inlay film comprising: a layer of dielectric film having a pattern of holes suitable to define selected regions to which particles will be deposited by electrostatic deposition; and a conductive element comprising polymer, which element comprises (a) a conductive film laminated against the dielectric film or (b) a conductive film embedded within the holes, the portion of the conductive element appearing within the holes comprising conductive inlays, wherein the conductive element is adapted to contact one or more electrode pads and provide electrical potentials at the selected regions, and wherein the dielectric film electrically isolates the selected regions. The invention can be used to deposit measured amounts of particles on the selected regions of substrates, wherein the amounts of particles deposited on the selected regions can be measured amounts. The measured amounts can be of a medicament, forming a dosage unit. Or, for example, the conductive inlay film can comprise a diagnostic product with measured amounts of diagnostic reagent at two or more selected regions.

The invention also provides a method of electro-attractive deposition onto a substrate comprising: layering a conductive inlay film onto a surface of an electrostatic chuck comprising at least one electrode contacting the surface, wherein the conductive inlay film comprises conductive polymer effective to transmit potentials from the electrodes to the vicinity of selected regions of the conductive inlay film and dielectric film effective to electrically isolate the selected regions; applying a potential to the at least one electrode; directing particles toward the conductive inlay film; and selectively depositing particles at the selected regions. Note that the term "electrostatic chuck" indicates its use to attract charged powder/particles; such a chuck need not necessarily electrically adhere the substrate to which the powder/particles will be applied. The substrate can be layered on the chuck with, for example, vacuum or adhesive.

Further provided is a pharmaceutical, vitamin formulation, sweetener formulation, herbal formulation, veterinary formulation, or diagnostic product comprising: at least a portion of a conductive inlay film, the conductive inlay film comprising: a layer of dielectric film having a pattern of holes suitable to define selected regions to which particles will be deposited by electrostatic deposition; and a conductive element comprising polymer, which element comprises (a) a conductive film laminated against the dielectric film or (b) a conductive film embedded within the holes, the portion of the conductive element appearing within the holes comprising conductive inlays), the portion comprising a said inlay surrounded by the dielectric film; and a defined amount of pharmaceutical, vitamin, sweetener, herbal product, veterinary pharmaceutical or diagnostic agent selectively deposited on one or more said inlays.

DETAILED DESCRIPTION OF THE INVENTION

Figure 1A:
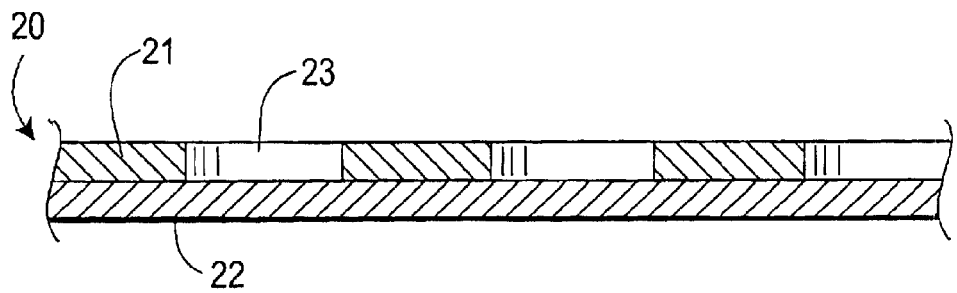
FIGS. 1A and 1B display a conductive inlay film according to the invention.
Figure 1B:
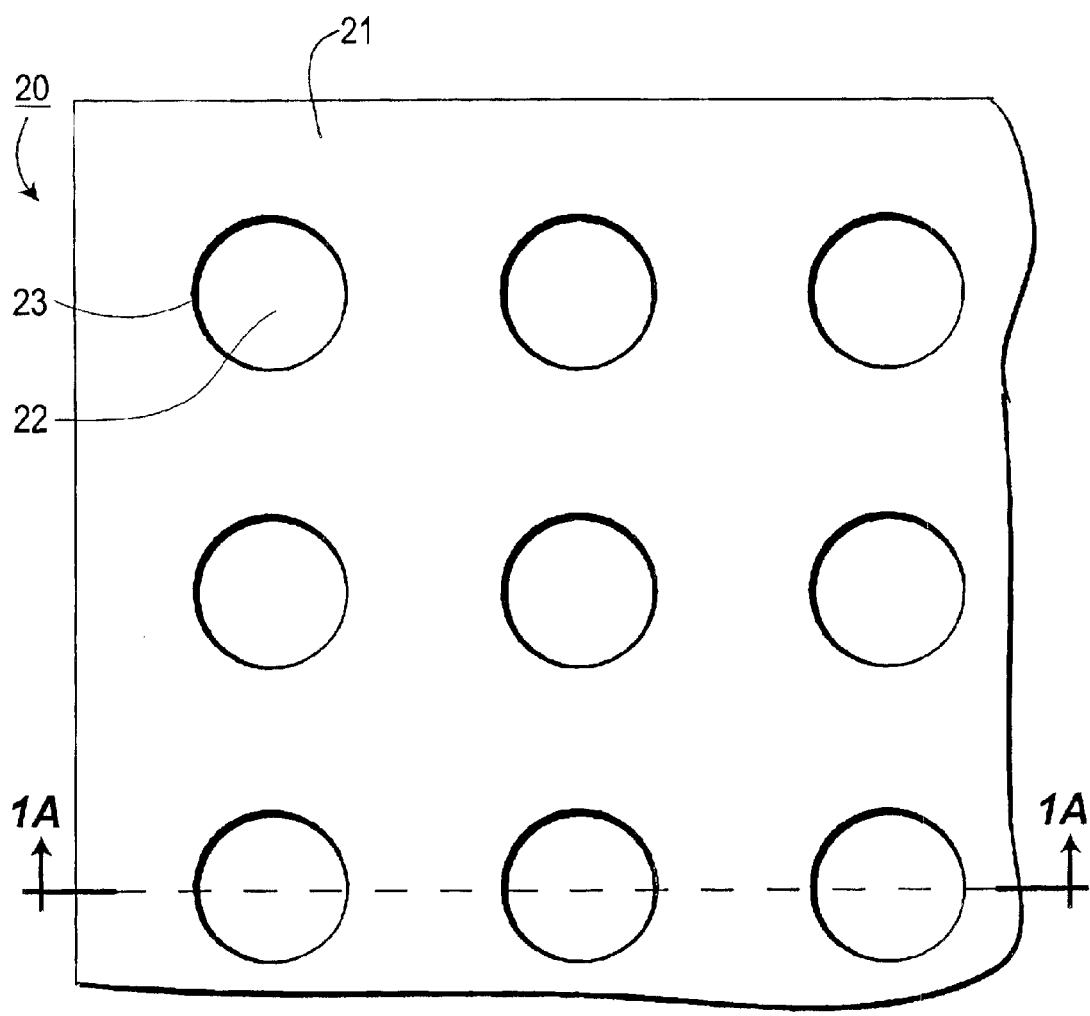

One illustrative embodiment of the invention is shown in FIG. 1. FIG. 1A shows a cross-section of conductive inlay film 20 having conductive film 22 laminated to dielectric film 21. The dielectric film 21 is of a relatively low conductivity and thickness as to allow selective attraction of charged particles to selected regions 23, while limiting any attraction of the particles to areas outside the selected region 23.

Suitable dielectric films include, for example, films of ethylcellulose, cellulose acetate phthalate, hydroxypropylmethyl cellulose (HPMC), hydroxypropylmethyl cellulose phthalate, hydroxypropyl cellulose (HPC), methyl cellulose, modified starch, protein (including, e.g. crosslinked gelatin), alginic acid, acrylic polymer (e.g., methyl methacrylate, ethyl acrylate, copolymers of methyl methacrylate, and ethyl acrylate, and the like, such as Eudragit™ acrylic copolymers), polyalkylene oxide (such as polyethylene oxide), polyvinyl alcohol, polyvinylpyrrolidone (PVP), crosslinked PVP, polylactide, poly(lactide-co-glycolide), non-woven fabric, paper, and the like. Film forming processes include casting of polymer solutions or dispersions and extrusion molding of polymer powders.

The conductive film is preferably formed of materials that are appropriate for human consumption. For certain materials, this preferred restriction means appropriate in the amount and dosing of the consumable product. Preferably, the conductive film is formed of a polymer which is itself conductive, or which provides a structural framework for a conductive material incorporated into the film. The conductive material can be, for example, a metallic weave, metal particles (such as particles of gold, silver or iron), carbon black particles, particles of other ionic species, and the like. The conductive material can also be a conductive polymer, such as gelatin or other proteinaceous material. Suitable polymers for imbedding conductive material include ethylcellulose, cellulose acetate phthalate, HPMC, hydroxypropylmethyl cellulose phthalate, HPC, methyl cellulose, modified starch, protein (including, e.g. crosslinked gelatin), alginic acid, acrylic polymer (e.g., methyl methacrylate, ethyl acrylate, copolymers of methyl methacrylate, and ethyl acrylate, and the like, such as Eudragit™ acrylic copolymers), polyalkylene oxide (such as polyethylene oxide), polyvinyl alcohol, PVP, crosslinked PVP, polylactide, poly(lactide-co-glycolide), non-woven fabric, paper, and the like. The water soluble polymer examples can be cast from a water solution, with the casting and drying conducted at a temperature above the lower critical solution temperature ("LCST"). The LCST for HPC, for example, is typically in the 50–55° C. range. Film forming processes again can include casting of polymer solutions or dispersions and extrusion molding of polymer powders.

Preferably, the conductive elements of the conductive inlay film, e.g., conductive film 22 or conductive inlay 32 (see below), have a resistivity of $10^5$ ohm/square or less, more preferably $10^4$ or $10^3$ ohm/square or less.

The selected regions 23 can be formed, for example, by cutting the dielectric film prior to laminating the film to the conductive film. The sizes of the selected regions 23 are, in pharmaceutical applications especially, for example from 1 mm to 10 mm in width or diameter.

The conductive inlay film of the invention is preferably flexible. The elements of the conductive inlay film on which particles are deposited are favorably water-swellable or dispersible, facilitating the dispersal or dissolution of deposited particles (see definition below) in appropriate aqueous solutions (e.g., acidic, basic or neutral, depending on the intended use of the conductive inlay film with deposited particles). Suitable thicknesses for the conductive inlay film include from 0.5 mil to 10 mil, more preferably 1.0 mil to 5 mil.

Figure 2A:
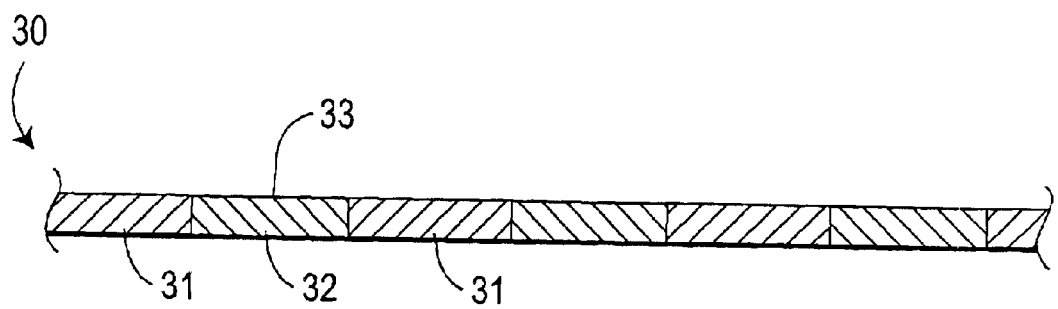
FIGS. 2A and 2B show another a conductive inlay film according to the invention.
Figure 2B:
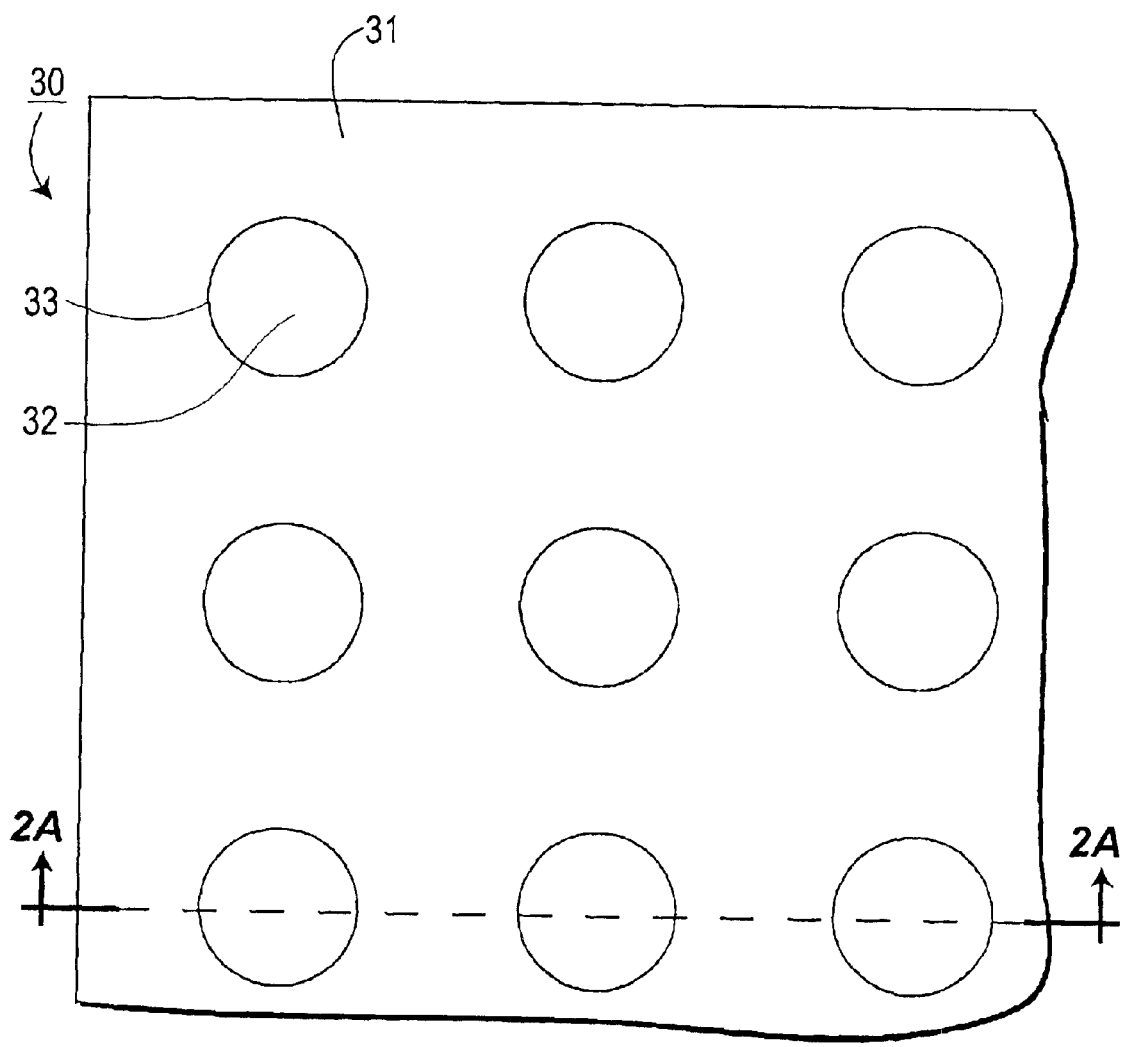

Another illustrative embodiment of the invention is shown in FIG. 2. FIG. 2A shows a cross-section of conductive inlay film 30 having conductive inlays 32 in dielectric film 31. The dielectric film 31 is of a relatively low conductivity and thickness as to allow selective attraction of charged particles to selected regions 33, while limiting any attraction of the particles to areas outside the selected region 33. This embodiment can be designed so that the conductive inlays 32 align with conductive pads on the surface of an electrostatic chuck. Again, the dielectric film is selected to maintain the electrical isolation of the selected regions such that particle-attracting fields are confined to these regions.

The embodiment of FIG. 2 can be formed, for example, by layering the dielectric film, on which holes corresponding to the selected regions have been formed, onto a release layer. A polymer solution or water-swellable gel, which can have conductive particles suspended therein, is used to fill the holes. Water-swellable gels-forming polymers include ethylcellulose, cellulose acetate phthalate, HPMC, hydroxypropylmethyl cellulose phthalate, HPC, methyl cellulose, modified starch, protein (including, e.g. crosslinked gelatin), alginic acid, acrylic polymer (e.g., methyl methacrylate, ethyl acrylate, copolymers of methyl methacrylate, and ethyl acrylate, and the like, such as Eudragit™ acrylic copolymers), polyalkylene oxide (such as polyethylene oxide), polyvinyl alcohol, PVP, crosslinked PVP, polylactide, poly(lactide-co-glycolide), non-woven fabric, paper, and the like. The solution, or the water-swelled gel are embedded in the dielectric film by, for example, drying in a humidity and temperature controlled chamber. The conductive inlay film so formed can now be peeled off the release layer.

It will be recognized that the embodiment of FIG. 2 can be laminated against a conductive film to form an embodiment that is a hybrid of the embodiments of FIG. 1 and FIG. 2.

It will be understood that the conductive inlay films of the invention can be used in methods of electrostatically depositing particles thereon. The use of electrostatic chucks for conducting such depositions, including methods of charging the particles (e.g., by induction or tribocharging) and measuring deposition amounts, are described in a number of patents and patent applications identified below. Deposition measurements can include optical measurement following deposition, and the use of electrical sensors that dynamically monitor deposition. One useful method of charging the particles is induction charging by passing the particles through a jet mill with conductive walls to which a potential is applied.

Figure 3:
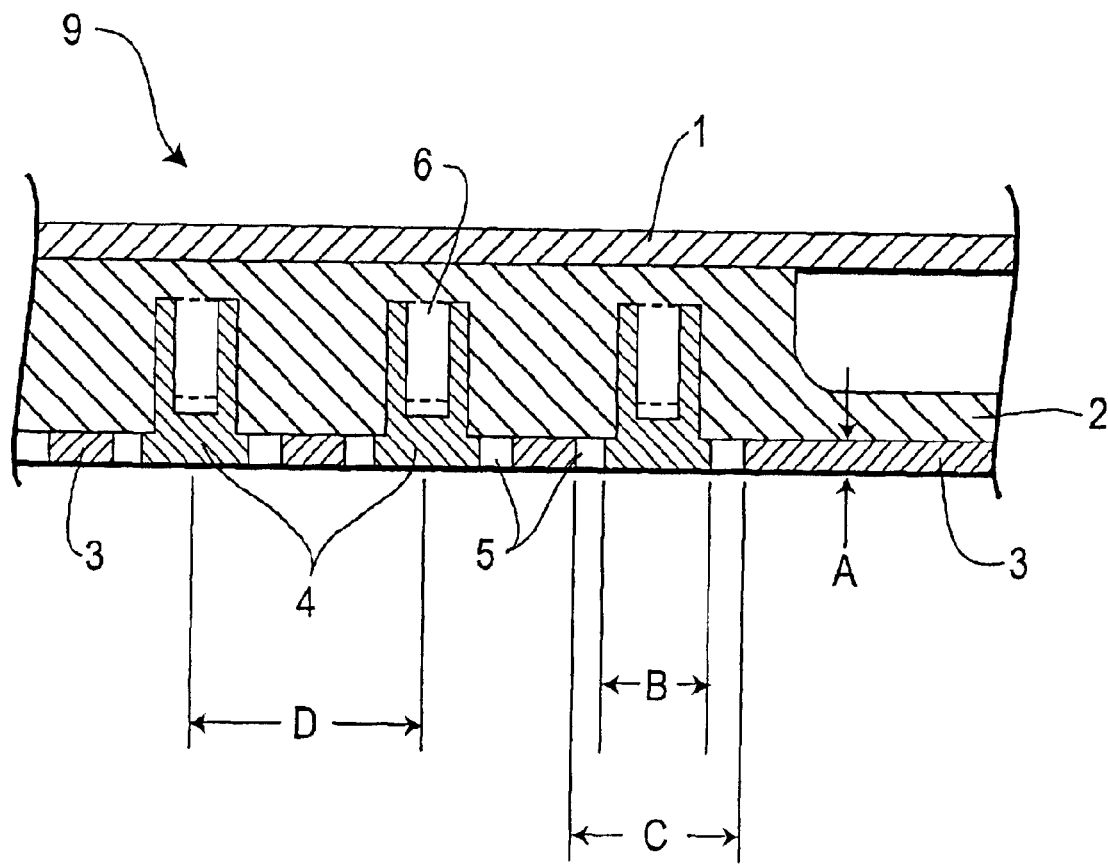
FIG. 3 shows an exemplary electrostatic chuck.

FIG. 3 shows a cross-section of a coplanar chuck 9 where deposition electrodes 4 are separated from shield electrodes 3 by dielectric (preferably atmosphere) 5 with these features seated in base material 2. The deposition electrodes 4 are preferably formed of series 300 stainless steel. Deposition electrodes 4 contain a pin receptacle 6 for connection to circuit board 1. Base material 2 is made of a dielectric such as Noryl® polymer (GE Plastics, Pittsfield, Mass.). Noryl engineered plastics are modified polyphenylene oxide, or polyphenylene oxide and polyphenylene ether, resins. The modification of these resins involves blending with a second polymer such as polystyrene or polystyrene/butadiene. By varying the blend ratio and other additives, a variety of grades are produced. Unmodified, these polymers are characterized by regular closely spaced ring structures (phenyl groups) in the main molecular chain. This feature along with strong intermolecular attraction causes extreme stiffness and lack of mobility. The shield electrodes 3 can be made from a conductive material (such as 300 series stainless steel) adhered to the base material 2, for example by an adhesive or a double-sided, rubber-based adhesive tape. The annular gaps that are the preferred embodiment of dielectric 5 can be made by drilling a series of holes in the conductor layer that will form the shield electrodes 3. The deposition electrodes 4 can be, for example, pressed or glued into the base material. The assembly is preferably ground to create a flat, coplanar surface, for example within a tolerance of 0.0002 inches. Where dielectric 5 is atmosphere (that atmosphere in which the electrostatic chuck operates), preferably the portion of the dielectric separation of the electrodes comprising atmosphere is sufficient so that in use the upper plane of the electrostatic chuck aligned with dielectric 5 discharges completely between depositions. Such an amount of dielectric separation is "substantial" separation.

Such an electrostatic chuck can be simply modified with the techniques described to incorporate electrically isolated shield electrodes that can be separately connected to control electronics to provide the sensing circuits described above. Dimension A can be, for example, 0.01 inch; Dimension B can be, for example, 0.157 inch; Dimension C can be, for example, 0.236 inch; Dimension D, the pitch between pixels, can be, for example, 0.3543 inch. The electrostatic chuck can be operated, for example, with a voltage of ~700 or ~1,400 V applied to the deposition electrodes.

The measured amounts of particles or grains deposited by the invention can be useful in a number of contexts, such as pharmaceuticals, vitamin formulations, sweetener formulations, herbal formulations, veterinary formulations, diagnostic products (with defined quantities of control substances or diagnostic reagents), and the like.

Glossary

The following definitions are provided to facilitate understanding of certain terms used frequently herein:

"Particles" for deposition are, for the purposes of this application, aggregates of molecules, typically of at least about 3 nm average diameter, such at least about 500 nm or 800 nm average diameter, and are preferably from about 100 nm to about 5 mm, for example, about 100 nm to about 500 μm. Particles are, for example, particles of a micronized powder, or polymer structure that can be referred to as "beads." Beads can be coated, have adsorbed molecules, have entrapped molecules, or otherwise carry other substances.

"Electro-attractive dry deposition" refers to methods that use electrical forces to attract or deposit charged particles to a surface.

"Dosage unit" refers to a convenient amount of a given substance. For pharmaceuticals, the term typically refers to amounts that add up to, using a convenient number of dosage units, an appropriate dosage of a pharmaceutical.

The invention described herein can be used in conjunction with a number of devices and methods described by applicants or those working with applicants. For example, the "Electrostatic Sensing Chuck Using Area Matched Electrodes" patent of Sun et al., U.S. Pat. No. 6,370,005, and the "Device for the Dispersal and Charging of Fluidized Powder" patent of Sun et al., U.S. Pat. No. 6,491,241 can be used in conjunction with the invention. Other devices or methods that can be used with various aspects of the present invention include, for example, the methods for use of transporter chucks, acoustic bead dispensers and other powder-manipulating devices set forth in Sun, "Chucks and Methods for Positioning Multiple Objects on a Substrate," U.S. Pat. No. 5,788,814, issued Aug. 4, 1998; Sun et al., "Electrostatic Chucks and a Particle Deposition Apparatus Therefor," U.S. Pat. No. 5,858,099, issued Jan. 12, 1999; Pletcher et al., "Apparatus for Electrostatically Depositing a Medicament Powder Upon Predefined Regions of a Substrate," U.S. Pat. No. 5,714,007, issued Feb. 3, 1998 (see, also U.S. Pat. No. 6,007,630, issued Dec. 28, 1999); Sun et al., "Method of Making Pharmaceutical Using Electrostatic Chuck," U.S. Pat. No. 5,846,595, issued Dec. 8, 1998; Sun et al., "Acoustic Dispenser," U.S. Pat. No. 5,753,302, issued May 19, 1998; Sun, "Bead Transporter Chucks Using Repulsive Field Guidance," U.S. Pat. No. 6,098,368, issued 1, Aug. 2000; Sun, "Bead Manipulating Chucks with Bead Size Selector," U.S. Pat. No. 5,988,432, issued Nov. 23, 1999; Sun, "Focused Acoustic Bead Charger/Dispenser for Bead Manipulating Chucks," U.S. Pat. No. 6,168,666, issued 2, Jan. 2001; Sun et al., "AC Waveforms Biasing For Bead Manipulating Chucks," U.S. Pat. No. 6,149,774, issued 21, Nov. 2000.; Sun et al, "Method for Clamping a Planar Substrate," U.S. Pat. No. 6,399,143; Poliniak et al., "Dry Powder Deposition Apparatus," U.S. Pat. No. 6,063,194, issued 16, May 2000; and "Pharmaceutical Product," U.S. Pat. No. 6,303,143. Additional powder-handling devices, including a cone-shaped cloud chamber, are described in O'Mara et al., "Article Comprising a Diffuser with Flow Control Features," U.S. Pat. No. 6,44,033.

All publications and references, including but not limited to patents and patent applications cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The following examples further illustrate the present invention, but of course, should not be construed as in any way limiting its scope.

EXAMPLE 1

Two-layer Polymer Film of Ethylcellulose (EC) and HPMC

The two-layer polymer film consists of a hydrophobic ethylcellulose (EC) film layer and a hydrophilic HPMC film layer. The first step: Cast EC dispersion plasticized with triacetin or other plasticizers over a Mylar film to make the ethylcellulose (EC) layer. Drying is conducted in a temperature/humidity-controlled chamber at 55° C. and 35% RH. The second step: Cast HPMC solution over the resulting EC film, making the hydrophilic layer. Drying is conducted at 28° C. and 45% RH. The two-layer film is then peeled off from the Mylar film.

EXAMPLE 2

Polymer film Attached with Conductive Domains

Disperse carbon black into hydroxypropyl cellulose polymer solution to make a conductive polymer film. Disk-like film portions are punched out from the film. The conductive disks are then layered over an EC film (as in Example 1) and sealed by ultrasonic welding. The EC film has high surface resistivity (targeted at 2.6E+12 ohm/square at 20% RH and 1.2E+12 ohm/square at 30% RH, respectively).

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A conductive inlay film-with deposited particles comprising:

a flexible film, which comprises:

a layer of dielectric film having a pattern of holes suitable to define selected regions for selectively depositing particles by electrostatic deposition; and a conductive element comprising polymer, which element comprises (a) a conductive film laminated against the dielectric film or (b) a conductive film embedded within the holes, the portion of the conductive element appearing within the holes comprising conductive inlays; and particles selectively deposited on the selected regions, wherein the conductive element is adapted to reversibly contact one or more electrode pads and provide electrical potentials at the selected regions, and wherein the dielectric film electrically isolates the selected regions.

2. The conductive inlay film of claim 1, wherein the amounts of particles deposited on the selected regions are a measured amounts.

3. The conductive inlay film of claim 1, wherein the particles comprise a medicament and each selected region defines a dosage unit.

4. The conductive inlay film of claim 1, wherein the particles comprise a diagnostic reagent and the conductive inlay film comprises a diagnostic product with measured amounts of diagnostic reagent at two or more selected regions.

5. The conductive inlay film of claim 1, wherein the conductive element comprises (a) a conductive film laminated against the dielectric film.

6. The conductive inlay film of claim 1, wherein the conductive element comprises (b) a conductive film embedded within the holes, the portion of the conductive element appearing within the holes comprising conductive inlays.

7. A method of electro-attractive deposition onto a substrate comprising:

reversibly layering a flexible conductive inlay film onto a surface of an electrostatic chuck comprising at least one electrode contacting the surface, wherein the conductive inlay film comprises conductive polymer effective to transmit potentials from the electrodes to the vicinity of selected regions of the conductive inlay film and dielectric film effective to electrically isolate the selected regions;

applying a potential to the at least one electrode;

directing particles toward the conductive inlay film; and selectively depositing particles at the selected regions.

8. A pharmaceutical, vitamin formulation, sweetener formulation, herbal formulation, veterinary formulation, or diagnostic product comprising:

at least a portion of a conductive inlay film formed of materials that are appropriate for human consumption, the conductive inlay film comprising:

a layer of dielectric film having a pattern of holes suitable to define selected regions to which particles will be deposited by electrostatic deposition; and a conductive element comprising polymer, which element comprises (a) a conductive film laminated against the dielectric film or (b) a conductive film embedded within the holes, the portion of the conductive element appearing within the holes comprising conductive inlays, the portion comprising a said inlay surrounded by the dielectric film; and a defined amount of pharmaceutical, vitamin, sweetener, herbal product, veterinary pharmaceutical or diagnostic agent selectively deposited on one or more said conductive inlays.

9. A pharmaceutical dosage unit according to claim 8.

10. A vitamin dosage unit according to claim 8.

11. A sweetener administration unit according to claim 8.

12. A herbal dosage unit according to claim 8.

13. A veterinary dosage unit according to claim 8.

14. A diagnostic product according to claim 8.

15. The conductive inlay film according to claim 1, wherein the conductive inlays are arrayed in a repetitive pattern.

16. The conductive inlay film according to claim 1, wherein the flexible conductive inlay film is 0.5 mil to 10 mil in thickness.

17. The conductive inlay film according to claim 1, wherein the flexible conductive inlay film is 1.0 mil to 5 mil in thickenss.

18. The method of claim 7, wherein the particles are selectively deposited on said conductive inlays which are arrayed in a repetitive pattern.

19. The method of claim 7, wherein the reversible layering is conducted with conductive inlay film that is formed of materials that are appropriate for human consumption.

20. The pharmaceutical, vitamin formulation, sweetener formulation, herbal formulation, veterinary formulation, or diagnostic product according to claim 8, wherein the portion of conductive inlay film comprises conductive inlays arrayed in a repetitive pattern.

21. The pharmaceutical, vitamin formulation, sweetener formulation, herbal formulation, veterinary formulation, or diagnostic product according to claim 8, wherein the conductive inlay film is flexible.

22. The conductive inlay film of claim 1, wherein the conductive film is formed of materials that are appropriate for human consumption.

23. The conductive inlay film of claim 1, wherein particles are deposited on the selected regions by electro-attractive deposition.

* * * * *